United States Patent [19]
Mori

[11] Patent Number: 5,970,780
[45] Date of Patent: Oct. 26, 1999

[54] OXYGEN SENSOR

[75] Inventor: Rentarou Mori, Kasugai, Japan

[73] Assignee: Toyota Jidosha Kabushiki Kaisha, Aichi, Japan

[21] Appl. No.: 08/898,784

[22] Filed: Jul. 23, 1997

[30] Foreign Application Priority Data

Aug. 21, 1996 [JP] Japan ................................. 8-219933

[51] Int. Cl.⁶ .................................................. G01N 7/00
[52] U.S. Cl. ........................................................ 73/23.31
[58] Field of Search ........................ 73/23.31; 204/426, 204/425, 424

[56] References Cited

U.S. PATENT DOCUMENTS

| | | | |
|---|---|---|---|
| 4,170,530 | 10/1979 | Watabe et al. | 204/195 S |
| 4,359,374 | 11/1982 | Sano et al. | 204/195 S |
| 4,655,892 | 4/1987 | Satta et al. | 204/192.15 |
| 4,940,528 | 7/1990 | Oki et al. | 204/427 |
| 4,946,577 | 8/1990 | Shibata et al. | 204/427 |
| 5,480,535 | 1/1996 | Kondo et al. | 204/425 |

FOREIGN PATENT DOCUMENTS

| | | |
|---|---|---|
| A-3-264857 | 11/1991 | Japan. |
| A-5-307015 | 11/1993 | Japan. |
| A-5-322820 | 12/1993 | Japan. |

*Primary Examiner*—Hezron Williams
*Assistant Examiner*—Jay L. Politzer
*Attorney, Agent, or Firm*—Oliff & Berridge, PLC

[57] ABSTRACT

An oxygen sensor comprising a substrate made of a metal oxide and electrodes on the surface of the substrate coming into contact with a reference gas and the surface coming into contact with a measured gas, wherein the electrode on at least one of the surfaces of the substrate comprises a laminate structure of a primary particle formed by metallizing a precious metal onto the surface of the metal oxide particle. According to this construction, the porosity of the electrodes can be increased and the size of the interface with the gas can be. Further, deterioration of the electrodes can be prevented even under conditions which generate thermal sintering. In other words, the response as the well as the durability can be improved.

9 Claims, 3 Drawing Sheets

OXYGEN SENSOR

BACKGROUND OF THE INVENTION

1. Field of the Invention

This invention relates to an oxygen sensor. More particularly, the present invention relates to an oxygen sensor having improved heat resistance and response due to improved electrodes.

2. Description of the Related Art

Oxygen sensors have been used widely to control the fuel cost in various combustion furnaces, to control an air-fuel ratio to allow a ternary catalyst for processing an exhaust gas of an automobile to function effectively, and to control an oxygen concentration in a metal refining process. A semiconductor type (titania type) oxygen sensor which utilizes electron conductivity of oxide semiconductors and a solid electrolyte type (zirconia type) oxygen sensor utilizing ion conductivity of a solid electrolyte are known as such oxygen sensors.

The semiconductor oxygen sensor detects the oxygen concentration in the exhaust gas by utilizing the property of the titania device as an oxide semiconductor in that its electric resistance changes depending on the oxygen concentration, or in other words, its electric resistance is as high as an oxide insulating material when the oxygen concentration is high, but becomes low because oxygen in the oxide disappears when the oxygen partial pressure is low, and the resistance value drops due to the resulting lattice defect of oxygen.

On the other hand, the solid electrolyte oxygen sensor uses zirconia ($ZrO_2$) stabilized by calcia (CaO), yttria ($Y_2O_3$), etc. as an oxygen ion conductive solid electrolyte, and has electrodes on both surfaces of this solid electrolyte, that is, the surface coming into contact with a reference gas and the surface coming into contact with a measured gas. The measured gas such the exhaust gas, for example, is brought into contact with one of these electrodes and the reference gas such as air, for example, is brought into contact with the other electrode. Conduction of the oxygen ions does not occur under the state where the oxygen concentration of the measured gas is substantially equal to the oxygen concentration of the reference gas, and no voltage develops between these electrodes.

However, the oxygen ions move from the reference gas side to the measured gas side inside the solid electrolyte when the oxygen concentration of the measured gas is low. At this time, the oxygen molecule carries the electrons from the electrode on the boundary surface between the platinum electrode and the solid electrolyte on the reference gas side, and the electrons are entrapped as the oxygen ions into the solid electrolyte. As a result, the reference gas side is charged to positive. On the other hand, the oxygen ions moving inside the solid electrolyte emit the electrons at the electrode on the measured gas side, and become oxygen atoms. The oxygen atoms occurring in this way on the measured gas side are consumed as they react with carbon monoxide and hydrocarbons and are emitted in the oxygen molecule state. In this way, the voltage develops between the two electrodes, and the oxygen concentration is detected by utilizing this electromotive force.

As described above, the electrodes for electrically picking up the detection signal corresponding to the oxygen concentration are disposed on the surface of the sensor device in all of the various types of oxygen sensors described above. The electrode has been produced in the past by applying a precious metal paste such as a platinum (Pt) paste to a substrate and baking the substrate (for example, refer to Japanese Unexamined Patent Publication (Kokai) No. 3-264857).

In such an oxygen sensor, the electrodes must be made porous in order to allow a flow of the oxygen gas. Further, the boundary surfaces between the electrode, the substrate and the reference gas or the measured gas must be increased. When the electrode is produced by applying the precious paste, however, porosity cannot be increased to a high level, and the problem develops in that sintering of the precious metal particles proceeds depending on the baking temperature and the boundary surface with the measured gas, that is, the operation area, drops. According to a chemical plating method, on the other hand, a porous electrode can be formed, it is true, but the formation of a thick electrode is difficult, and only an electrode having a thickness of about 1 to about 2 $\mu m$ can be formed. If the electrode has such a limited thickness, sintering occurs because the temperature of the measured gas is as high as 700 to 800° C. and the operation area drops.

SUMMARY OF THE INVENTION

In an oxygen sensor comprising a substrate made of a metal oxide and electrodes formed on the surface of this substrate coming into contact with a reference gas and on its other surface coming into contact with a measured gas, an oxygen sensor according to the present invention for solving the problems described above employs the construction wherein the electrode on at least one of the surfaces of the substrate has a laminated structure of particles obtained by metallizing a precious metal on the surface of the metal oxide particles. When the electrode has such a structure, the porosity of the electrode can be increased, a flow passage for the oxygen gas can be secured, and sintering at a high temperature can be prevented. Furthermore, the boundary surfaces between the gas, the electrodes and the substrate can be increased, and the operation area of the oxygen sensor can be increased. As a result, the heat resistance as well as the response of the oxygen sensor can be improved.

DESCRIPTION OF THE PREFERRED EMBODIMENTS

Hereinafter, the present invention will be explained with reference to the accompanying drawings.

Figure 1:
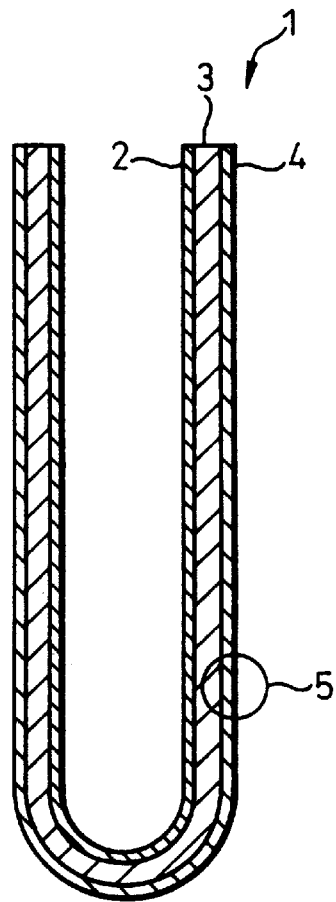
FIG. 1 is a substantial sectional view of an oxygen sensor according to the present invention.

FIG. 1 is a sectional view showing schematically an oxygen sensor according to the first embodiment of the present invention.

Referring to FIG. 1, reference numeral 1 denotes a concentration cell type oxygen sensor, and reference numeral 3 denotes a cylindrical metal oxide substrate the distal end of which is closed. Reference numeral 2 denotes an inner electrode formed on the inner surface of the substrate, and reference numeral 4 denotes an outer electrode formed on the outer surface of the substrate. Oxygen ion conductive solid electrolytes that are generally used for the concentration cell type oxygen sensors are used as the metal oxide for producing this substrate. Zirconia ($ZrO_2$) stabilized by calcia (CaO), yttria ($Y_2O_3$), etc, is a preferred example of such an oxygen ion conductive solid electrolyte. The inner electrode of such an oxygen sensor is brought into contact with a reference gas such as air, and the outer electrode is brought into contact with a measured gas such as an exhaust gas. An electromotive force corresponding to an oxygen partial pressure ratio of the reference gas and the measured gas develops between both of the electrodes.

Figure 2:
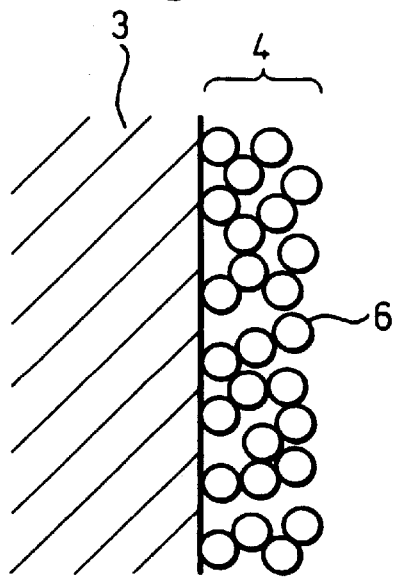
FIG. 2 is an enlarged sectional view of an electrode portion of the oxygen sensor according to the present invention.
Figure 3:
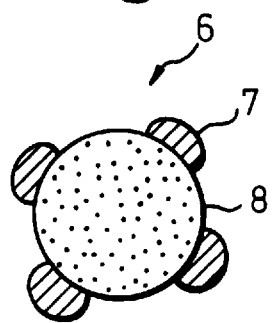
FIG. 3 is an enlarged sectional view of a primary particle that constitutes the electrode of the oxygen sensor according to the present invention.

FIG. 2 is an enlarged sectional view showing schematically the portion denoted by reference numeral 5 in FIG. 1. Here, the electrode 4 comprises a laminate structure of a plurality of primary particles 6 formed by metallizing a precious metal onto metal oxide particles. FIG. 3 shows the structure of this metallized primary particle 6. This primary particle 6 is formed by metallizing the metal oxide particle 8 with the precious metal particle 7 by vacuum deposition, electroless plating, sputtering, and so forth. Besides stabilized zirconia as the oxygen ion conductive solid electrolyte described above, gamma-alumina, spinel and various others can be used as the metal oxide. Platinum, gold, silver, rhodium, palladium, etc, that have been used generally for the electrode, can be used as the precious metal.

As shown in FIG. 2, the electrode of the oxygen sensor according to the present invention comprises a laminate structure of the primary particles 6 formed by metallizing the precious metal 7 onto the surface of the metal oxide particle 8. Therefore, in comparison with the electrodes formed by the conventional paste method or plating method, porosity can be made by far higher, and the specific surface area of the electrode can also be increased. Consequently, the area of the interface between the gas and the electrode can be increased. When the oxygen ion conductive solid electrolyte is used as the metal oxide particle 8, the area of the interface between the solid electrolyte and the gas can be increased.

To accomplish the effects of the present invention, the size of the primary particle 6 is preferably not greater than dozens of microns. When the primary particle 6 is greater than 100 microns, for example, the space inside the electrode 4 becomes large, and impurities other than the gas are likely to be entrapped. Such impurities adhere to the precious metal and lower the activity of the electrode. Therefore, large impurities can be prevented from being entrapped into the space inside the electrode by limiting the size of the primary particle to not greater than dozens of microns. On the other hand, if this primary particle is too small, the particles become so dense that a sufficient porosity cannot be accomplished. At times, oxygen is entrapped inside the electrode, and the electrode cannot respond to the change of the gas concentration. Further, it is technically difficult to form the particles of the metal oxide having a size below the micron order. From the aspects of easy passage of the gas and difficult passage of the impurities, the size of the primary particle 6 is preferably from several microns to dozens of microns and particularly preferably, from 20 to 30 microns. The precious metal particle 7 is preferably not greater than 10 microns from the aspect of ease of sintering.

The laminate structure of the primary particle 6 can be formed on the substrate 3 by an ordinary method. It can be formed, for example, by mixing the primary particles in an organic solvent, dipping the sensor device into this solution under the mixed state so as to cause the solvent and the primary particles to adhere to the surface of the sensor device, and then drying the sensor device. Baking is then carried out to evaporate only the organic solvent, and the primary particles are allowed to adhere by sintering. Though the electrode on the outer surface has the laminate structure of the primary particles in this embodiment, the inner surface, too, may have such a laminate structure. Though this embodiment represents a so-called "cup type device", the size and the shape of the device substrate are not particularly limited. For example, the shape may be a cylinder, a square cylinder, a flat sheet, and so forth, and the substrate may be shaped in a customary manner. Further, though this embodiment represents the concentration cell type oxygen sensor, the present invention can be applied to other oxygen sensors such as a semiconductor type oxygen sensor.

Figure 4:
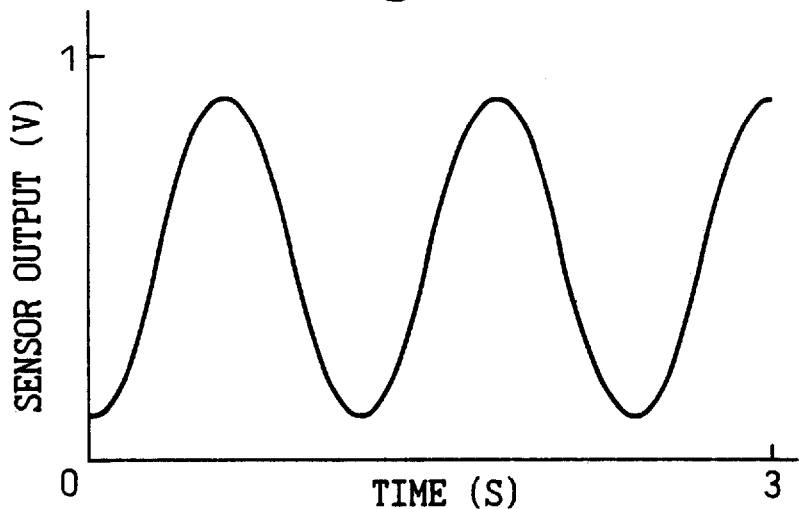
FIG. 4 is a graph showing a sensor response waveform of the oxygen sensor according to the present invention.
Figure 5:
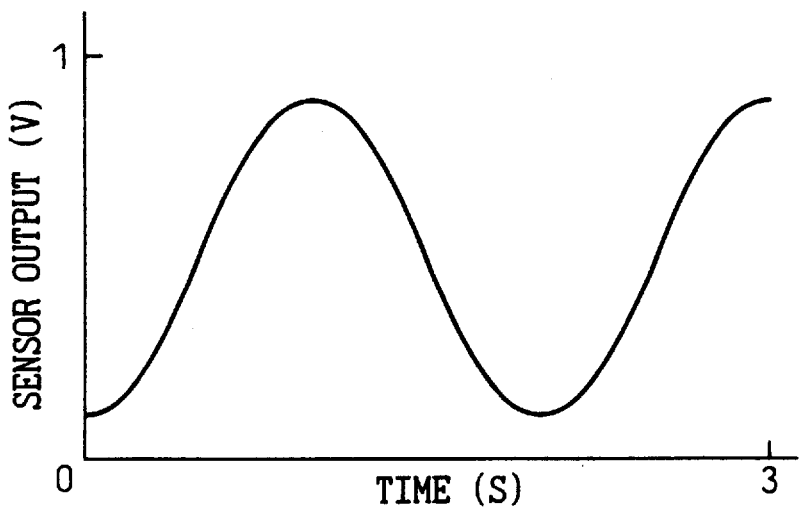
FIG. 5 is a graph showing a sensor response waveform of an oxygen sensor having electrodes formed by a paste method.

FIG. 4 shows the change with time of the output of the oxygen sensor having such a construction according to the present invention. As can be seen clearly from this graph, the sensor output of the oxygen sensor of the present invention changes sinusoidally and regularly with time, and a sufficient output is produced. In the case of the oxygen sensor having the electrodes formed by the plating method, too, the time change of its output exhibits the response waveform similar to that of the oxygen sensor of the present invention. In the case of the oxygen sensor having the electrodes formed by the paste method, however, the output is substantially similar to that of the present invention but its response is lower.

Figure 6:
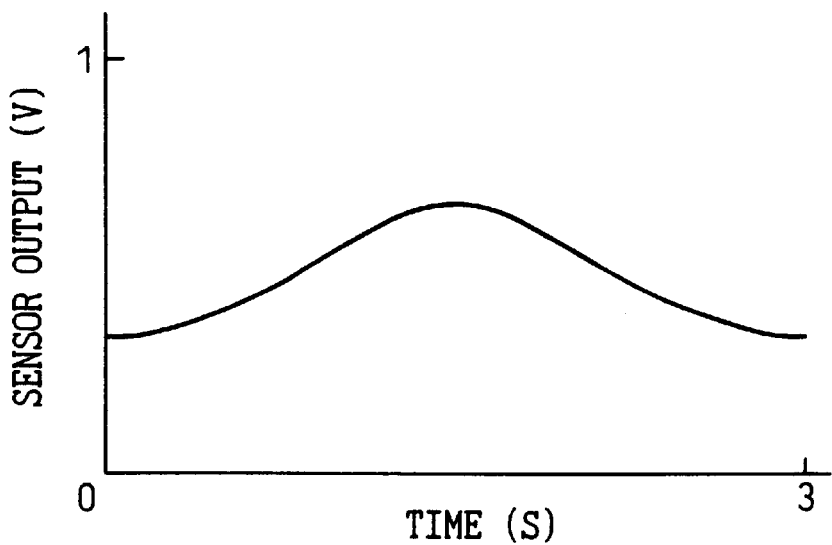
FIG. 6 is a graph showing a sensor response waveform of the oxygen sensor having electrodes formed by a plating method, after thermal sintering.

Each of these oxygen sensors is heat-treated at 900° C. to cause thermal sintering, and the time change of its output is measured in the same way. The change can be hardly observed in the oxygen sensor of the present invention and the oxygen sensor having the electrodes formed by the paste method, but the output and response drop in the oxygen sensor having the electrodes formed by plating method, as shown in FIG. 6.

Figure 7:
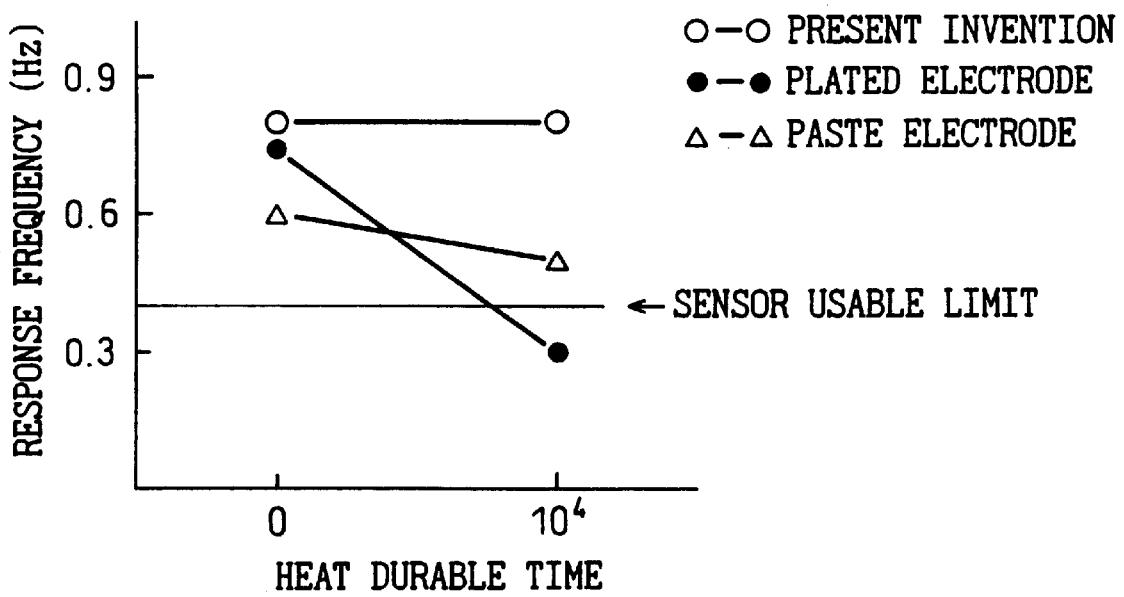
FIG. 7 is a graph showing response frequency of the oxygen sensor of the present invention, a response frequency of an oxygen sensor having electrodes formed by the paste method and the response frequency of the oxygen sensor having electrodes formed by the plating method, before and after the thermal durability test, respectively.

The response frequency of each of these oxygen sensors before and after the thermal treatment is measured, and the result is shown in FIG. 7. As can be seen clearly from FIG. 7, the oxygen sensor according to the present invention exhibits a high response frequency before and after the thermal durability test, and has excellent heat resistance. In the oxygen sensor the electrodes of which are formed by the plating method, the precious metal is sintered by the heat-treatment and forms so-called large "islands". As a result, the electrode is partly cut off and the output drops. In contrast, in the oxygen sensor according to the present invention, sintering of the precious metal on the primary particle and sintering of the precious metal between the particles occur due to the heat-treatment. Consequently, the large islands of the previous metal are not formed, the electrode is not fragmented, and the drop of the output does not occur, either.

According to the present invention described above, the electrode can be constituted by a laminate structure of the primary particle 6 formed by metallizing the precious metal particle 7 onto the metal oxide particle 8. Accordingly, the porosity of the electrode can be increased, and the size of the interface with the gas can be increased. Further, deterioration of the electrode can be prevented even under the condition where thermal sintering occurs. In other words, both the response and the durability can be improved.

What is claimed is:

1. An oxygen sensor comprising: (1) a substrate comprising a metal oxide, the substrate having a first surface that comes into contact with a reference gas and a second surface that comes into contact with a gas to be measured, and (2) electrodes formed on both the first and second surfaces of said substrate, the electrode on at least one of the first and second surfaces of said substrate consisting predominately of a plurality of primary particles each having a laminate structure comprising a metal oxide particle and a precious metal particle, wherein the precious metal particle is metallized over the entire surface of the metal oxide particle.

2. An oxygen sensor according to claim 1, wherein said substrate comprises an oxygen ion conductive solid electrolyte comprising zirconium oxide as a principal component.

3. An oxygen sensor according to claim 1, wherein said metal oxide particle is zirconia, gamma-alumina or spinel.

4. An oxygen sensor according to claim 1, wherein said precious metal particle is platinum, gold, silver, rhodium or palladium.

5. An oxygen sensor according to claim 1, wherein each said primary particle has a particle size of 20 to 30 microns.

6. An oxygen sensor according to claim 1, wherein said precious metal particle has a particle size of not greater than 10 microns.

7. An oxygen sensor according to claim 1, wherein each said primary particle is formed by metallizing said precious metal particle onto said metal oxide particle by a vacuum deposition method, an electroless plating method or a sputtering method.

8. An oxygen sensor according to claim 6, wherein each said primary particle has a particle size of 20 to 100 microns.

9. An oxygen sensor according to claim 1, wherein each said primary particle comprises more than one precious metal particle metallized to the surface of the metal oxide particle.

* * * * *